United States Patent [19]

Moyer

[11] Patent Number: 4,510,447
[45] Date of Patent: Apr. 9, 1985

[54] INSPECTION APPARATUS FOR ELECTROMAGNETICALLY DETECTING FLAWS IN THE WALL OF A PIPE

[75] Inventor: Mark C. Moyer, Missouri City, Tex.

[73] Assignee: Exxon Production Research Co., Houston, Tex.

[21] Appl. No.: 315,329

[22] Filed: Oct. 26, 1981

[51] Int. Cl.³ .................... G01N 27/72; G01R 33/12
[52] U.S. Cl. ................................ 324/225; 324/240; 324/262
[58] Field of Search ............... 324/225, 234, 235, 236, 324/237, 238, 239, 240, 241, 242, 243, 262

[56] References Cited

U.S. PATENT DOCUMENTS

| | | | |
|---|---|---|---|
| 1,428,833 | 9/1922 | Bindschedler | 324/228 |
| 2,077,380 | 4/1937 | Drake | 324/217 |
| 3,422,346 | 1/1969 | Hammer | 324/241 X |
| 3,495,166 | 2/1970 | Lorenzi et al. | 324/237 |
| 3,555,412 | 1/1971 | Fowler | 324/235 |
| 3,579,099 | 5/1971 | Kanbayashi | 324/235 |
| 3,710,236 | 1/1973 | Halsey et al. | 324/235 |
| 4,105,972 | 8/1978 | Smith | 324/220 |
| 4,188,577 | 2/1980 | Mhatre et al. | 324/220 |
| 4,258,319 | 3/1981 | Shimada et al. | 324/237 |
| 4,281,230 | 7/1981 | Naylor | 200/61.58 R |
| 4,297,636 | 10/1981 | Link et al. | 324/240 |
| 4,386,318 | 5/1983 | Burbank et al. | 324/225 |

FOREIGN PATENT DOCUMENTS

| | | |
|---|---|---|
| 0039793 | 4/1981 | European Pat. Off. |
| 0065325 | 4/1982 | European Pat. Off. |
| 1471595 | 4/1977 | United Kingdom |
| 1498218 | 1/1978 | United Kingdom |
| 1539313 | 1/1979 | United Kingdom |
| 2012966 | 8/1979 | United Kingdom |
| 1562631 | 3/1980 | United Kingdom |
| 2071331 | 9/1981 | United Kingdom |
| 1604188 | 12/1981 | United Kingdom |

Primary Examiner—Gerard R. Strecker
Assistant Examiner—Walter E. Snow
Attorney, Agent, or Firm—E. Eugene Thigpen

[57] ABSTRACT

Apparatus for detecting flaws in the wall of a ferromagnetic pipe is disclosed. The apparatus comprises an electromagnetic having poles in slideable contact with the surface of the wall of the ferromagnetic pipe to form a closed magnetic circuit and means for electrically connecting the coil of the electromagnetic to an input source of alternating current whereby a fluctuating magnetic field is induced generally axially through the wall of the pipe between the poles of the electromagnetic. The apparatus also comprises means adjacent the surface of the wall of the pipe between the poles of the electromagnet for sensing a leakage of the axial magnetic field therefrom and generating a signal corresponding to a sensed portion of the leakage. The apparatus further comprises means for electrically connecting the sensing means to a readable output device.

10 Claims, 3 Drawing Figures

4,510,447

INSPECTION APPARATUS FOR ELECTROMAGNETICALLY DETECTING FLAWS IN THE WALL OF A PIPE

FIELD OF THE INVENTION

This invention relates to detecting flaws in the wall of a ferromagnetic pipe, and more particularly to apparatus for detecting flaws in a ferromagnetic, oil field tubular.

BACKGROUND OF THE INVENTION

Currently, the magnetic particle method is used to identify flaws in the wall of an oil field tubular such as, for example, tubing for the flow of oil or gas, casing for cement-out formation, and drill pipe. For convenience, an oil field tubular will be referred to hereinafter as a pipe. When pipe is originally produced, it is inspected for flaws at an automated station. The term "flaws", as used herein, includes any discontinuities or irregularities in the walls of the pipe such as, for example, seams, laps, and slugs. When the pipe reaches the field, the magnetic particle inspection is used in the field to verify that the delivered pipe has no flaws. Furthermore, the magnetic particle inspection is the only method available to identify flaws in large-diameter pipe that will not fit through the automated stations. The magnetic particle method is accomplished by magnetizing the wall of the pipe or providing it with a residual magnetic field and thereafter dusting fine particles of iron or iron oxides on a region of the wall to ascertain whether or not there are any flaws of the type referred to above. While experience has shown results obtained using the magnetic particle method are generally better than most, increased flaw-detection sensitivity is necessary. Additionally, this type of inspection has serious limitations inasmuch as the wall of the pipe must first be cleansed of any oil, dirt, corrosion, or the like. The most serious limitation of the magnetic particle method is that the inspection is very dependent on the visual acuity and experience of the inspector.

SUMMARY OF THE INVENTION

The instant invention is based on the discovery of apparatus for detecting flaws in the wall of a ferromagnetic pipe. The apparatus comprises an electromagnet, having poles which are in slidable contact with the surface of the wall of the ferromagnetic pipe to form a closed magnetic circuit, means for electrically connecting the coil of the electromagnet to an input source of alternating current to induce a fluctuating magnetic field through the wall of the pipe, and means adjacent the surface of the wall of the pipe between the poles of the electromagnet for sensing leakage of the magnetic field therefrom and generating a signal corresponding to a sensed portion of the leakage. The apparatus also includes means for electrically connecting the sensing means to a readable output device. Since no magnetic powder is needed, the invention eliminates the requirement of cleaning before inspection, thus reducing the amount of time required to inspect a pipe. Furthermore, because the apparatus is in slideable contact with the surface of the pipe, the invention is easier to manipulate both longitudinally and circumferentially along the surface thereof. Thus, the invention can cover larger surface areas of the wall of the pipe to further reduce the amount of time required to inspect a pipe. Most importantly, however, the invention minimizes the dependency on the visual acuity and experience of the inspector and is more sensitive to smaller flaws as will be discussed hereinbelow.

DETAILED DESCRIPTION OF THE INVENTION

Figure 1:
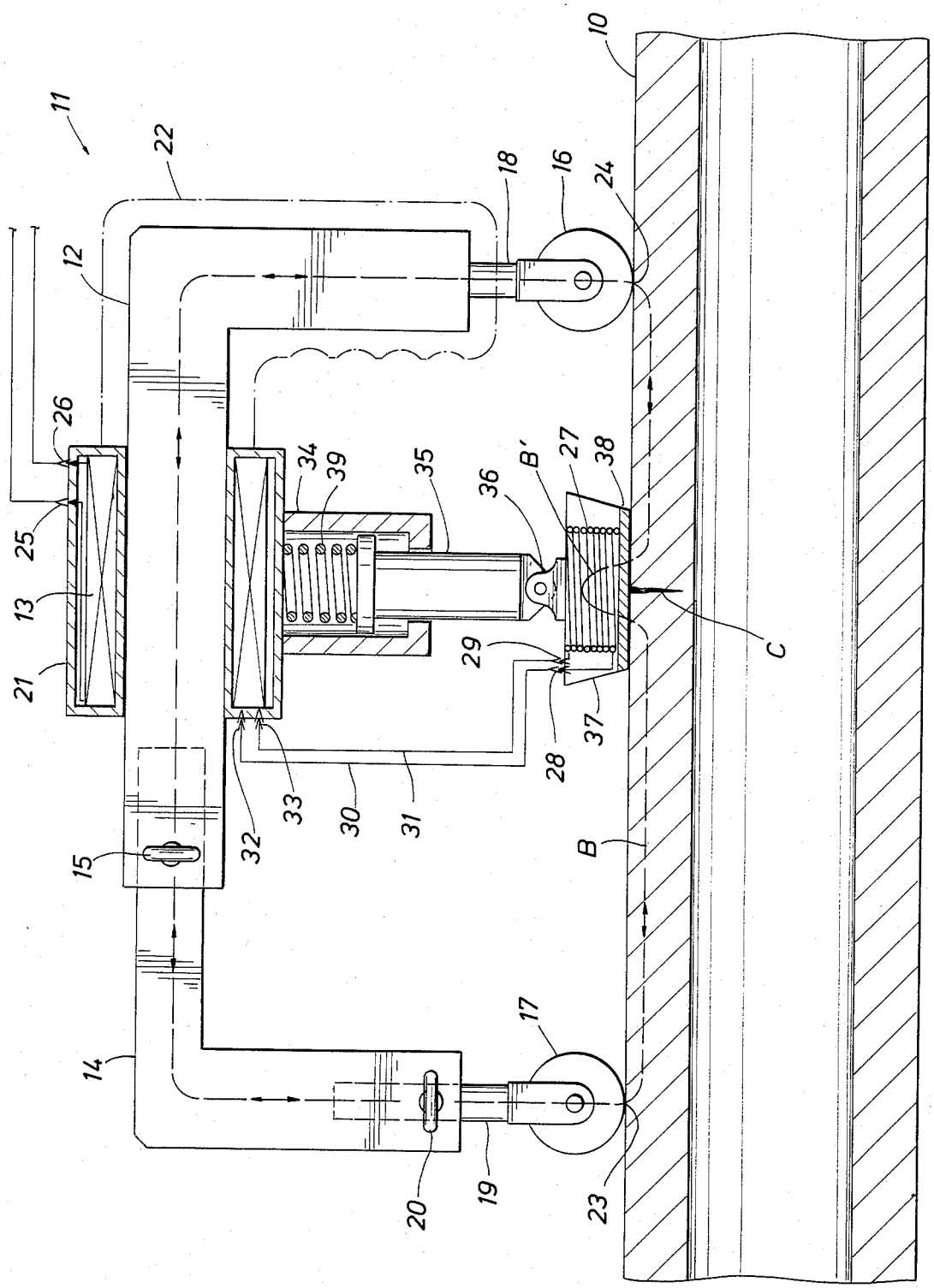
FIG. 1 is a partially schematic, vertical sectional view of apparatus for detecting flaws in the wall of a ferromagnetic pipe in accordance with the invention.

Referring now in more detail to FIG. 1, apparatus for detecting flaws in the wall of a ferromagnetic pipe 10 is indicated generally at 11. The apparatus 11 comprises an electromagnet which includes an L-shaped core 12 and coil 13 wound thereon. One end of the core 12 extends axially from the coil 13 and is slideably connected to an L-shaped bracket 14 so that the length of the apparatus 11 is adjustable. A bolt 15 is mounted at the end of the core 12 so that it fixes the length of the apparatus 11 when tightened against the bracket 14 slideably inserted within the core 12. The other end of the core 12 and the other end of the bracket 14 extend in a direction generally radially from the longitudinal axis of the coil 13 toward the surface of the pipe 10 and support metal wheels 16 and 17, respectively, on which the apparatus 11 rides. The wheels 16 and 17 permit the operator to rapidly cover large longitudinal surface areas of the wall of the pipe 10. The wheel 16 supported by the core 12 is connected thereto by a metal bar 18 and the wheel 17 supported by the bracket 14 is slideably connected thereto by another metal bar 19 so that the pitch of the apparatus 11 also can be adjusted. Another bolt 20 is mounted at the end of the bracket 14 so that it fixes the pitch of the apparatus 11 when tightened against the bar 19 slideably inserted within the bracket 14. Plastic casings 21 and 22 shroud the coil 13 and the core 12, respectively, so that an operator can more easily move the apparatus 11 along the surface of the pipe 10 to facilitate inspection.

The bracket 14, the bars 18 and 19, and the wheels 16 and 17, as well as the core 12, are all ferromagnetic and form a magnetizing circuit in which the wheels 16 and 17 function as the poles 23 and 24 of the electromagnet. When the wheels 16 and 17 are placed in contact with the surface of the wall of the pipe 10, the magnetizing circuit forms a closed magnetic circuit with the wall of the pipe 10. The reluctance of the magnetic circuit is greatly reduced because the air gaps between adjacent ferromagnetic elements of the magnetizing circuit, as well as between the magnetizing circuit and the wall of the pipe 10, have been minimized. The air gaps between the magnetizing circuit and the wall of the pipe 10 is minimized by fabricating the wheels 16 and 17 so that the contacting surfaces thereof are essentially concave to conform to the surface of the wall of the pipe 10. The wheels 16 and 17 are also interchangeable with other pairs of wheels having different concavity to accommodate the particular pipe being inspected. When the coil 13 is connected to a source of alternating current (not shown) at terminals 25 and 26, a fluctuating magnetic field is generated through the magnetizing circuit and the wall of the pipe 10 along a path approximated by a dashed line B. Since the reluctance of the closed magnetic circuit has been greatly reduced, the magnetic field B generated by the coil 13 is correspondingly increased. It is desirable to maximize the magnitude of the magnetic field B in order to detect small flaws in the wall of the pipe 10 such as, for example, the crack indicated at C. The crack C creates a discontinuity in the permeability of the wall of the pipe 10 which causes a leakage B' in the magnetic field B.

The apparatus 11 also comprises means adjacent the surface of the wall of the pipe 10 between the poles 23 and 24 of the electromagnet for sensing the leakage B' of the magnetic field B and generating a signal corresponding to a sensed portion of the leakage B'. In the illustrated embodiment, the sensing means is a solenoid 27 having its axis aligned perpendicular to the surface of the wall of the pipe 10 and connected at terminals 28 and 29 to a volt meter, strip chart recorder, or similar device (not shown) which can be mounted directly on the case 21. Leads 30 and 31 connect the terminals 28 and 29, respectively, to terminals 32 and 33, respectively, for the volt meter. However, it is to be understood, that the solenoid 27 can be oriented in any direction to sense a portion of the leakage B'. It is also to be understood that other means responsive to the magnetic field B can be used such as, for example, Hall elements, magnetometers, magnetodiodes, and similar devices. The fluctuating leakage B' generated by the alternating current induces a voltage into the coil 27 corresponding to the component of the leakage B' extending radially from the surface of the wall of the pipe 10.

The apparatus 11 further comprises mounting means mechanically connected to the electromagnet at the underside of the casing 21 for supporting and yieldingly urging the solenoid 27 toward the surface of the wall of pipe 10. The mounting means comprises a cylinder 34 and a piston 35 slideably positioned therein. The cylinder 34 has a flanged open end and a closed end connected to the casing 21 of the electromagnet to form a cavity therein. The piston 35 has a headed end slideably fitted within the cavity of the cylinder 34 and is held in the cavity of the cylinder 34 by the flanged open end thereof. The other end of the piston 35 extends axially through the flanged open end of the cylinder 34 and terminates at a joint 36. A housing 37 encloses the coil 27 and supports the terminals 28 and 29. The housing 37 has one end connected to a wear-resistant shoe 38 end in slideable contact with the surface of the wall of the pipe 10 and the other end rotatably connected to the joint 36 to accommodate for the pitch variations in the apparatus 11 when the bar 19 is adjusted. A compression spring 39 is disposed within the cavity of the cylinder 34 between the closed end thereof and the headed end of the piston 35. The spring 39 causes the piston 34 to yieldingly urge the housing 37 against the surface of the wall of the pipe 10 to hold it in position thereon.

Figure 2:
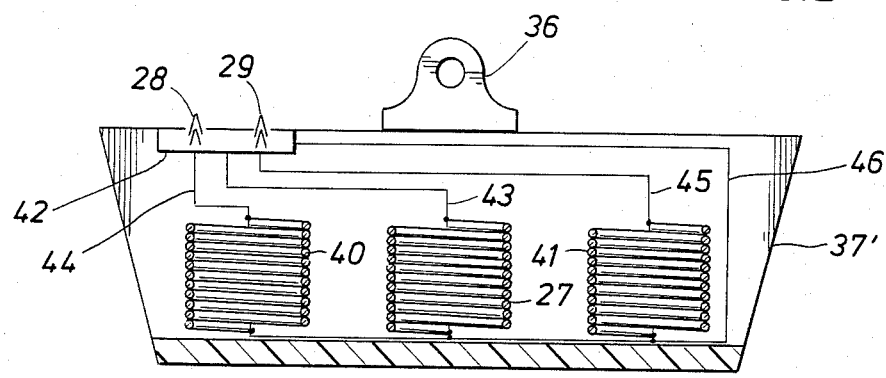
FIG. 2 is a partially schematic, vertical sectional view of detecting means and compensating means of apparatus for detecting flaws in the wall of a ferromagnetic pipe in accordance with the invention.

During experimentation with the apparatus 11, it has been discovered that a residual leakage emanates from the wall of the pipe 10 even in the absence of a flaw therein. To obtain more precise detection with the solenoid 27, the voltage induced by the residual leakage is measured and subtracted from the voltage induced in the solenoid 27 because of the flaw C. This is accomplished by positioning compensating solenoids on both sides of the detecting solenoid 27 along a line between the poles 23 and 24 of the electromagnet and electrically connecting the compensating solenoids with the detecting solenoid 27 so that the average voltage induced in the compensating solenoids is subtracted from the voltage induced in the detecting solenoid 27. Referring in more detail to FIG. 2, a housing 37' represents the embodiment of the housing 37 (FIG. 1) as represented by similar numerals where appropriate. The housing 37' is supported by the joint 36 and enclosed the detecting solenoid 27 and compensating solenoids 40 and 41 of similar electrical characteristics and orientation as described hereinabove. The detecting and compensating solenoids 27, 40 and 41 are connected to an adder/subtracter circuit 42 by wires 43, 44 and 45, respectively, and grounded thereto by a wire 46. The output from the circuit 42 is provided to the terminals 28 and 29.

Figure 3:
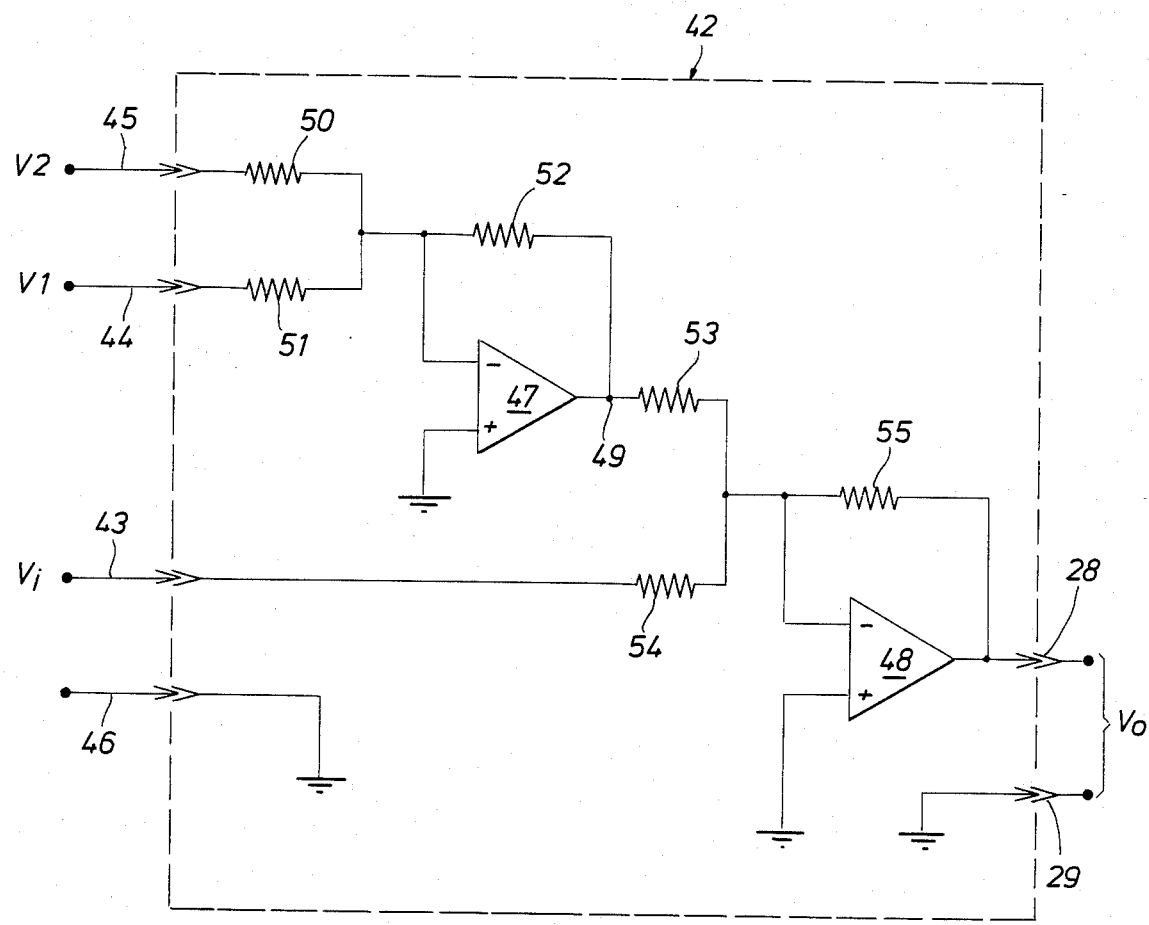
FIG. 3 is an electrical schematic of means for subtracting the average of the signals provided by the compensating means from the signal provided by the detecting means and generating a corresponding signal in accordance with the invention.

Referring to FIG. 3, the adder/subtractor circuit 42 comprises a first adder which incorporates an operational amplifier 47 that averages and changes the polarity of the voltages V1 and V2 induced in the compensating solenoids 40 and 41, respectively, and a second adder which incorporates an operational amplifier 48 that sums the negative output from the operational amplifier 47 of the first adder at a node 49 to the voltage $V_i$ induced in the detecting solenoid 27. Loading resistors 50 and 51 each having a resistance of R/ohms are connected from the inverting terminal of the operational amplifier 47 to the compensating solenoids 40 and 41, respectively, by the wires 44 and 45, respectively. The voltages V1 and V2 are averaged by selecting the feedback resistor 52 that has a resistance approximately one-half that of the loading resistors 50 and 51, or approximately 0.5 R/ohms, so that the output of the operational amplifier 47 of the first adder circuit at the node 49 is approximately equal to the following quantity: $[-0.5(V1+V2)]$. Loading resistors 53 and 54 each having a resistance of R/ohms are connected from the inverting terminal of the operational amplifier 48 to the node 49 and to the detecting solenoid 27 by the wire 43, respectively. Therefore, when a feedback resistor 55 is selected that has a resistance of R/ohms, the output voltage $V_o$ from the operational amplifier 48 of the second adder circuit at terminals 28 and 29 is approximately represented by the following equation:

$$V_o = -[V_i - 0.5(V1 + V2)].$$

Thus, the two adder circuits function together as an adder/subtractor circuit. Although the polarity of the output voltage $V_o$ can be reversed, the polarity of the signal produced when a flaw is detected in the wall of the pipe 10 is not critical.

It will be apparent that various changes may be made in details of construction from those shown in the attached drawings and discussed in conjunction therewith without departing from the spirit and scope of this invention as defined in the appended claims. For example, the apparatus 11 can be used to detect flaws in any piece of ferromagnetic pipe regardless of the specific application. It is, therefore, to be understood that this invention is not limited to the specific details shown and described.

What I claim is:

1. Apparatus for detecting flaws in the wall of a ferromagnetic pipe, comprising:

an electromagnet comprising a coil, two ferromagnetic L-shaped members, a first arm of each L-shaped member being in axial alignment with said coil and in sliding engagement with each other, means for securing said first arms in a selected position with respect to each other, the second arm of each L-shaped member extending generally radially from the longitudinal axis of the coil, a pair of ferromagnetic wheels attached to the ends of said second arms, said wheels functioning as poles of the electromagnet and having concave surfaces adapted to conform to the surface of the wall of a pipe, at least one of said wheels being connected to one of said second arms by a connective means having an adjustable length, said electromagnet forming a closed magnetic circuit when said wheels are in contact with the surface of the wall of the ferromagnetic pipe;

means for electrically connecting the coil of said electromagnet to an input source of alternating current whereby a fluctuating magnetic field is generated through the wall of the pipe between the poles of said electromagnet;

detecting means adjacent the surface of the wall of the pipe between the poles of said electromagnet for sensing leakage of the magnetic field therefrom and generating a signal corresponding to a sensed portion of the leakage;

compensating means adjacent the surface of the wall of the pipe, one between said detecting means and each pole of said electromagnet for sensing residual leakage of the magnetic field from said electromagnet and generating signals corresponding to a sensed component of the residual leakage;

means for averaging the signals from said compensating means and providing a signal corresponding to the reverse polarity of the resultant average;

means for adding the output signal from said averaging means to the signal from said detecting means, whereby the output signal therefrom corresponds to the difference between the signal from said detecting means and the average of the signals from said compensating means; and, means for electrically connecting the signal from said adding means to a readable output device.

2. Apparatus as recited in claim 1, wherein said detecting means and said compensating means are solenoids.

3. Apparatus as recited in claim 1 or 2, further comprising mounting means mechanically connected to said electromagnet for supporting and yieldingly urging said detecting means and said compensating means toward the surface of the wall of the pipe.

4. Apparatus as recited in claim 3, wherein said mounting means comprises:

a cylinder having a flanged open end and a closed end mechanically connected to said electromagnet to form a cavity therein;

a piston having a headed end slideably fitted within the cavity of said cylinder and restrained therein by the flanged open end thereof, and the other free end extending axially through the flanged open end of the cylinder;

a housing enclosing said detecting means and said compensating means therein, said housing having one end in slideable contact with the surface of the wall of the pipe and the other end connected to the free end of said piston; and, a compression spring disposed within the cavity of said cylinder between the closed end thereof and the headed end of said piston, whereby the piston yieldingly urges said housing against the surface of the wall of the pipe.

5. Apparatus for detecting flaws in the wall of a ferromagnetic pipe, comprising:

an electromagnet comprising a coil, two ferromagnetic L-shaped members, a first arm of each L-shaped member being in axial alignment with said coil and in sliding engagement with each other, means for securing said first arms in a selected position with respect to each other, the second arm of each L-shaped member extending generally radially from the longitudinal axis of the coil, a pair of ferromagnetic wheels attached to the ends of said second arms, said wheels functioning as poles of the electromagnet and having concave surfaces adapted to conform to the surface of the wall of a pipe, at least one of said wheels being connected to one of said second arms by a connective means having an adjustable length, said electromagnet forming a closed magnetic circuit when said wheels are in contact with the surface of the wall of the ferromagnetic pipe;

means for electrically connecting the coil of said electromagnet to an input source of alternating current to generate a fluctuating magnetic field;

first detecting means for sensing a magnetic field and generating a signal corresponding thereto;

compensating detecting means positioned on each side of said first detecting means for sensing a magnetic field and generating signals corresponding thereto;

mounting means connected to the electromagnet and supporting said first detecting means and said compensating detecting means and adapted to yielding urge said first detecting means and compensating detecting means against the pipe surface so that said first detecting means is between said poles and said compensating detecting means are positioned on each side of said first detecting means and between said poles when the poles are placed against the pipe surface;

means for electrically combining the signals generated by the compensating detecting means with the signal generated by the first detecting means so that the average of the signals generated by the compensating detecting means is subtracted from the signal generated by the first detecting means thereby generating an output signal; and means for electrically connecting said output signal means to a readable output device.

6. Apparatus as recited in claim 5, wherein said first detecting means and said compensating detecting means are solenoids.

7. Apparatus as recited in claim 5 or 6, wherein said mounting means comprises:

a cylinder having a flanged open end and a closed end mechanically connected to said electromagnet to form a cavity therein;

a piston having a headed end slideably fitted within the cavity of said cylinder and restrained therein by the flanged open end thereof, and the other free end extending axially through the flanged open end of the cylinder;

a housing enclosing said first detecting means and said compensating detecting means therein, said housing having one end in slideable contact with the surface of the wall of the pipe and the other end connected to the free end of said piston; and a compression spring disposed within the cavity of said cylinder between the closed end thereof and the headed end of said piston, whereby the piston yieldingly urges said housing against the surface of the wall of the pipe.

8. Apparatus for detecting flaws in the wall of a ferromagnetic pipe, comprising:

an electromagnet comprising a coil, a ferromagnetic center portion extending axially through the coil, two ferromagnetic end portions extending on both sides of the coil from said center portion generally radially with respect to the axis of the coil, a ferromagnetic wheel connected to each of said end portions on the end away from the center portion to function as poles for the electromagnet when said wheels are in contact with the surface of the wall of the ferromagnetic pipe;

means for electrically connecting the coil of said electromagnet to an input source of alternating current to generate a fluctuating magnetic field;

first detecting means for sensing a magnetic field and generating a signal corresponding thereto;

compensating detecting means positioned on the side of said first detecting means for sensing a magnetic field and generating a signal corresponding thereto;

mounting means extending from said center portion of said electromagnet and supporting said first detecting means and said compensating detecting means, and adapted to yieldingly urge said first detecting means and compensating detection means against the pipe surface so that said first detecting means is between said poles and said compensating detecting means is positioned on the side of said first detecting means and between said poles when the poles are placed against the pipe surface;

means for subtracting the signal generated by the compensating means from the signal generated by the first detecting means thereby generating an output signal;

means for electrically connecting the output signal to a readable output device; and means for adjusting the spacing between the two end portions of said electromagnet and the length of at least one of said end portions so that said apparatus may be adapted for detecting flaws in different size pipe.

9. The apparatus of claim 8 wherein said wheels have concave surfaces to conform to the surface of the wall of the pipe.

10. Apparatus for detecting flaws in the wall of a ferromagnetic pipe, comprising:

an electromagnet comprising a coil, two L-shaped ferromagnetic members, a first arm of each L-shaped member being in axial alignment with said coil and in sliding engagement with each other, means for securing said first arms in a selected position with respect to each other, the second arm of each L-shaped member extending generally radially from the longitudinal axis of the coil, a pair of ferromagnetic wheels attached to the ends of said second arms, said wheels functioning as poles of the electromagnet and having concave surfaces adapted to conform to the surface of the wall of a pipe, at least one of said wheels being connected to a second arm by a connective means having an adjustable length, said electromagnet forming a closed magnetic circuit when said wheels are in contact with the surface of the wall of the ferromagnetic pipe;

means for electrically connecting the coil of said electromagnet to an input source of alternating current to generate a fluctuating magnetic field;

first detecting means for sensing a magnetic field and generating a signal corresponding thereto;

compensating detecting means positioned to the side of said first detecting means for sensing a magnetic field and generating a signal corresponding thereto;

mounting means connected to the electromagnet and supporting said first detecting means and said compensating detecting means and adapted to yielding urge said first detecting means and compensating detecting means against the pipe surface so that said first detecting means is between said poles and said compensating detecting means is positioned to the side of said first detecting means and between said poles when the poles are placed against the pipe surface;

means for electrically combining the signal generated by the compensating detecting means with the signal generated by the first detecting means so that the signal generated by the compensating detecting means is subtracted from the signal generated by the first detecting means thereby generating an output signal; and means for electrically connecting said output signal means to a readable output device.

* * * * *